(12) United States Patent
Jefferson

(10) Patent No.: US 8,257,329 B2
(45) Date of Patent: Sep. 4, 2012

(54) CONTRABAND RETRIEVAL DEVICE

(76) Inventor: Myron Jefferson, Newark, NJ (US)

( * ) Notice: Subject to any disclaimer, the term of this patent is extended or adjusted under 35 U.S.C. 154(b) by 362 days.

(21) Appl. No.: 12/545,942

(22) Filed: Aug. 24, 2009

(65) Prior Publication Data

US 2011/0046583 A1 Feb. 24, 2011

(51) Int. Cl.
*A61G 9/00* (2006.01)
(52) U.S. Cl. ................. 604/317; 4/450; 4/455
(58) Field of Classification Search ............ 4/289, 450, 4/455, 457, 318, 424, 452; 604/317
See application file for complete search history.

(56) References Cited

U.S. PATENT DOCUMENTS

| | | | | |
|---|---|---|---|---|
| 394,213 | A | * | 12/1888 | Scannell ........................... 4/289 |
| 454,826 | A | * | 6/1891 | Kynett ............................. 4/455 |
| 587,559 | A | * | 8/1897 | Riley ............................... 4/289 |
| 951,795 | A | * | 3/1910 | Berwanger ....................... 4/292 |
| 1,948,797 | A | * | 2/1934 | Nicolai ........................... 209/447 |
| 2,761,149 | A | * | 9/1956 | Kay ................................. 4/321 |
| 2,849,122 | A | * | 8/1958 | Roos .............................. 210/328 |
| 3,540,433 | A | | 11/1970 | Breckman |
| 3,597,771 | A | * | 8/1971 | Rickmeier, Jr. ................... 4/450 |
| 3,718,431 | A | | 2/1973 | Wild |
| 3,751,735 | A | * | 8/1973 | Sargent et al. .................... 4/318 |
| 4,101,279 | A | * | 7/1978 | Aslam ........................... 422/547 |
| 4,309,782 | A | | 1/1982 | Paulin |
| D267,273 | S | | 12/1982 | Paulin |
| 4,445,235 | A | | 5/1984 | Slover et al. |
| 4,472,269 | A | | 9/1984 | Swick |
| 4,866,793 | A | * | 9/1989 | Luedtke et al. ................ 4/300.3 |
| 5,331,973 | A | | 7/1994 | Fiedler et al. |
| 5,337,426 | A | | 8/1994 | Matusewicz et al. |
| 5,412,819 | A | | 5/1995 | Matusewicz et al. |
| 5,463,782 | A | | 11/1995 | Carlson et al. |
| 5,463,982 | A | | 11/1995 | Murphy |
| 5,701,844 | A | | 12/1997 | Murphy |
| 5,988,190 | A | * | 11/1999 | Borges ......................... 134/117 |
| 6,115,855 | A | | 9/2000 | Lorenzo |
| 6,135,307 | A | * | 10/2000 | Fahy ............................. 220/574 |
| 6,434,762 | B2 | | 8/2002 | Gordon |
| 6,491,814 | B1 | * | 12/2002 | Wheeler ....................... 210/164 |

(Continued)

FOREIGN PATENT DOCUMENTS

WO 9724971 A1 7/1997

OTHER PUBLICATIONS

*U.S. v. George*, 987 F.2d 1428 (9th Cir. 1993).*

(Continued)

*Primary Examiner* — Melanie J Hand
*Assistant Examiner* — Paula Craig
(74) *Attorney, Agent, or Firm* — Porzio, Bromberg & Newman, P.C.

(57) ABSTRACT

The present invention relates to a contraband retrieval device that can be used as a law enforcement tool that allows a law enforcement officer to retrieve items that are ingested or inserted into the body. A pan includes a plurality of apertures in a bottom thereof. Drug use, excrement can be retrieved in the pan and with water or a suitable liquid can be washed away leaving behind contraband substances which was contained in the excrement in the pan. The contraband substances can be retrieved from the pan and placed into evidence in a criminal investigation.

5 Claims, 2 Drawing Sheets

U.S. PATENT DOCUMENTS

| | | |
|---|---|---|
| 6,625,823 B1 | 9/2003 | Abbott |
| 6,640,355 B1 | 11/2003 | Samide |
| 6,802,085 B2 | 10/2004 | Catanescu et al. |
| D504,178 S | 4/2005 | Zolotnik |
| 7,395,784 B2 | 7/2008 | Hirokawa et al. |
| 7,837,939 B2* | 11/2010 | Tung et al. .................... 422/410 |
| 2005/0060797 A1* | 3/2005 | Gilmore et al. ................... 4/450 |
| 2006/0253968 A1* | 11/2006 | Mosler et al. ..................... 4/450 |
| 2009/0127207 A1* | 5/2009 | Okamoto et al. ............. 210/747 |

OTHER PUBLICATIONS

Kalideen, Nalisha, Condom record is a hard act to swallow, IOL News, Sep. 15, 2002.*

United Press International, Cops wait 3 weeks for swallowed cocaine, Apr. 29, 2009.*

* cited by examiner

CONTRABAND RETRIEVAL DEVICE

BACKGROUND OF THE INVENTION

1. Field of the Invention

The present invention relates in general to law enforcement and in particular to a contraband retrieval device to easily retrieve items that are ingested or inserted into the body.

2. Description of Related Art

Conventional devices to collect feces appear are known. U.S. Pat. No. 6,640,355 describes an article for collecting human feces. U.S. Pat. No. 6,434,762 describes a stool collecting apparatus.

U.S. Pat. No. 3,540,433 describes a feces strainer for use in easily and simply collecting a stool specimen, and is characterized by its ability to pass liquid constituents while retaining semisolid and solid constituents in a substantially nonadhesive manner so as to facilitate the removal of solid feces specimen constituents from the strainer. In a preferred form, the feces strainer comprises a shallow receiving bag having a strainer means at the bottom taking the form of netting material made of a substantially liquid-impervious plastic fiber material, thus facilitating the washing, sterilization, and quick drying thereof, and also the previously mentioned, nonadhesive functional characteristics thereof with respect to solid and semisolid feces specimen constituents. In a preferred form the netting material may be made of a double layer configuration having slightly offset and thus effectively size-reduced, complete through-apertures through the double layers thereof, thus producing the effect of a filtering material having very small apertures while being made of a relatively inexpensive, easily obtained double layer form of netting material with each layer having substantially larger apertures. The strainer is provided with means for mounting it easily and simply on any of several different forms of conventional feces-receiving chambers to facilitate the stool collecting use thereof.

None of the prior art of which applicant is aware describes a contraband retrieval device for retrieving contraband from human feces. It is desirable to provide a contraband retrieval device that can easily retrieve items that are ingested or inserted into the body.

SUMMARY OF THE INVENTION

The present invention relates to a contraband retrieval device that can be used as a law enforcement tool that allows a law enforcement officer to retrieve items that are ingested or inserted into the body. A pan includes a plurality of apertures in a bottom thereof. During use, waste or excrement can be retrieved in the pan and with water or a suitable liquid can be washed away leaving behind in the pan contraband substances which were contained in the waste or excrement. The contraband substances can be retrieved from the pan and placed into evidence in a criminal investigation.

The contraband retrieval device has low manufacturing costs. The contraband retrieval device can be placed in any standard toilet, port-a-potty, bed pan, potty chair and the like and the individual can then be allowed to pass naturally any item contained in their body into the contraband retrieval device. The contraband retrieval device can be used in numerous circumstances where restroom facilities may not be available.

The invention will be more fully described by reference to the following drawings.

DETAILED DESCRIPTION

Figure 1:
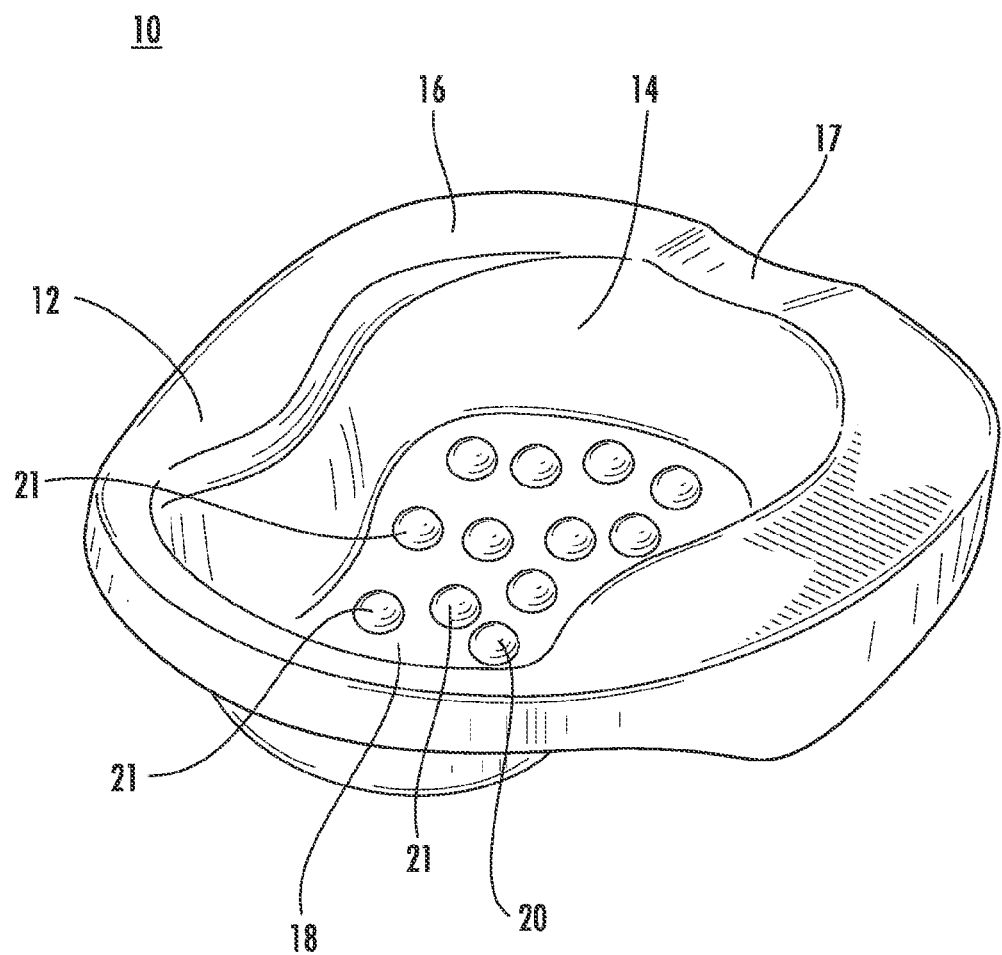
FIG. 1 is a schematic diagram of a contraband retrieval device in accordance with the teachings of the present invention.

Reference will now be made in greater detail to a preferred embodiment of the invention, an example of which is illustrated in the accompanying drawings. Wherever possible, the same reference numerals will be used throughout the drawings and the description to refer to the same or like parts.

FIG. 1 is a schematic diagram of contraband retrieval device 10 in accordance with the teachings of the present invention. Pan 12 includes wall 14 and rim 16 at top end 17 of wall 14. Wall 14 extends from bottom 18 of pan 12. Pan 12 can be in a shape and size for receiving waste such as human excrements. For example, pan 12 can have a size in the range of about 14⅜ inches by 11⅝ inches. Back height of wall 14 can be about 2⅞ inches and front height of wall 14 can be about 4¼ inches. Pan 12 can be placed on any standard toilet, port-a-potty, bed pan, bed pan chair and the like. Pan 12 can be formed of a plastic or metal material.

Figure 2:
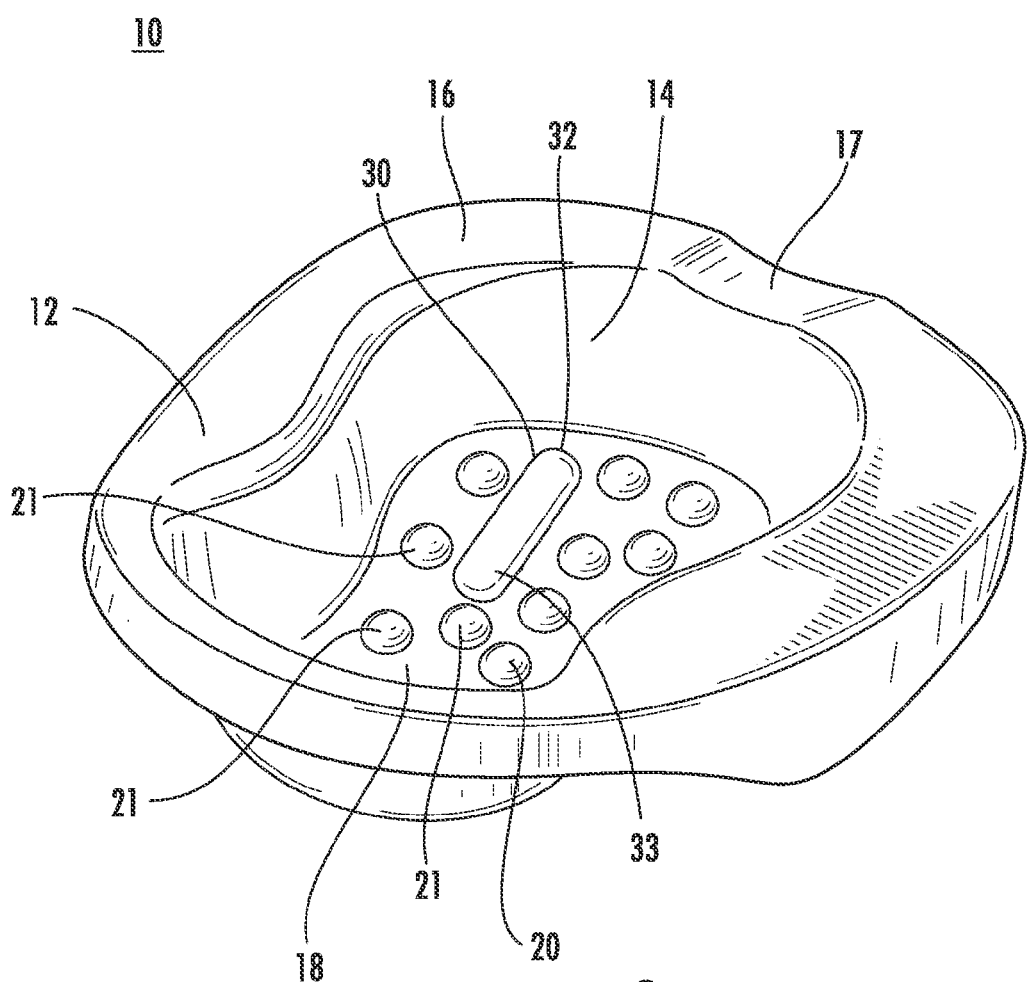
FIG. 2 is a schematic diagram of a contraband retrieval device during use.

A plurality of apertures 20 are formed in bottom 18 of pan 12. Apertures 20 have a size to retain contraband substances 30 in pan 12 while allowing waste or excrement when washed to exit pan 12 through apertures 20, as shown in FIG. 2. For example, contraband substances 30 can comprise bags 32 of contraband material 33. Contraband material 33 can include illegal drugs. Contraband substances 30 can be retrieved from pan 12 and placed into evidence in a criminal investigation.

Apertures 20 can have a size in the range of about 6 mm to about 8 mm or about ¼ inch to about 5/16 inch in diameter. In one embodiment, apertures 20 are symmetrically positioned with centers 21 positioned a distance of $L_1$, for example, about 108 mm or about 4¼ inches apart over bottom 18.

It is to be understood that the above-described embodiments are illustrative of only a few of the many possible specific embodiments, which can represent applications of the principles of the invention. Numerous and varied other arrangements can be readily devised in accordance with these principles by those skilled in the art without departing from the spirit and scope of the invention.

What is claimed is:

1. A method of retrieving an ingested substance that was ingested into the body of a user from waste of the user comprising the steps of:

providing to the user a retrieval device comprising a pan having a bottom and walls extending from said bottom and a plurality of apertures formed in said bottom, said apertures have a size in the range of about 6 mm to about 8 mm or about ¼ inch to 5/16 inch in diameter;

receiving waste from said user containing said ingested substance in said pan;

washing said pan with a liquid substance to remove all of said waste from said pan, said liquid substance and said waste passing through said apertures to remove said liquid substance and said waste from said pan to separate all of said waste from said ingested substance, said ingested substance is retained in said pan; and removing said ingested substance from said pan after all of said waste is removed in said washing step.

2. The method of claim 1 wherein said pan includes a rim at a top end of said wall.

3. The method of claim 1 wherein said apertures are symmetrically positioned within said bottom.

4. The method of claim 1 wherein said pan is formed of plastic.

5. The method of claim 1 wherein said liquid substance is water.

* * * * *